United States Patent [19]

Alburger

[11] 4,037,466
[45] July 26, 1977

[54] METHOD OF REGENERATING A GLYCOL-ETHER TYPE INSPECTION PENETRANT REMOVER BY SOLVENT EXTRACTION

[76] Inventor: James R. Alburger, 5007 Hillard Ave., La Canada, Calif. 91011

[21] Appl. No.: 735,681

[22] Filed: Oct. 26, 1976

Related U.S. Application Data

[63] Continuation-in-part of Ser. No. 606,285, Aug. 20, 1975, Pat. No. 3,988,924, which is a continuation-in-part of Ser. No. 577,323, May 14, 1975, Pat. No. 3,992,319, which is a continuation-in-part of Ser. No. 327,559, Jan. 29, 1973, abandoned.

[51] Int. Cl.$^2$ ............................................. G01N 19/02
[52] U.S. Cl. ........................................ 73/104; 134/10; 134/12
[58] Field of Search ...................... 134/10, 12; 73/104; 23/230 R, 230 C, 253 R, 253 C

[56] References Cited

U.S. PATENT DOCUMENTS

| | | |
|---|---|---|
| 3,558,882 | 1/1971 | Mlot-Fijalkowski ............. 73/104 X |
| 3,751,970 | 8/1973 | Alburger ........................... 73/104 X |
| 3,764,265 | 10/1973 | Mlot-Fijalkowski ............. 73/104 X |
| 3,926,044 | 12/1975 | Alburger ................................ 73/104 |

*Primary Examiner*—S. Leon Bashore
*Assistant Examiner*—Marc L. Caroff

[57] ABSTRACT

Water solutions of certain glycol-ether materials having resistance to extraction by halocarbon extraction solvents are used as solvent removers in an inspection penetrant process. Used solvent remover containing dissolved penetrant material and dyes is bubbled through a column of halocarbon solvent liquid, whereby the oily penetrant and dyes are selectively extracted leaving the glycol-ether/water mixture in a re-usable condition, the concentration of the glycol-ether in water remaining unchanged. Only a few glycol-ether liquids have been found to have the ability to resist extraction from their water solutions, and these substances are specified for use in the process of inspection penetrant usage, recovery and regeneration.

8 Claims, No Drawings

METHOD OF REGENERATING A GLYCOL-ETHER TYPE INSPECTION PENETRANT REMOVER BY SOLVENT EXTRACTION

This application is a continuation -in- part of copending application Ser. No. 606285, filed Aug. 20, 1975, for "Method of Regenerating an Inspection Penetrant Solvent," now U.S. Pat. No. 3,988,924, which application was a continuation-in-part of applciation Ser. No. 577,323, filed May 14, 1975, for "Inspection Penetrant Process Using Solvency-Inhibited Remover Compositions," now U.S. Pat. No. 3,992,319, which application was a continuation-in-part of application Ser. No. 327,559, filed Jan. 29, 1973 for "Solvency-Inhibited Remover Compositions and Process for Inspection Penetrants," now abandoned.

RELATED PATENTS AND PATENT APPLICATIONS

U.S. Pat. No. 3,107,298, for "APPARATUS FOR THE MEASUREMENT OF FLUORESCENT TRACER SENSITIVITY."

U.S. Pat. No. 3,311,479, for "PENETRANT INSPECTION PROCESS AND COMPOSITIONS."

U.S. Pat. No. 3,341,705, for "METHOD OF CONTROLLING THE THICKNESS OF APPLIED THIN LIQUID FILMS USING DYE TRACERS."

U.S. Pat. No. 3,386,920, (now Re-26,888) for "PROCESS FOR FLUORESCENCE DETECTION OF EXTREMELY THIN TRACER FILMS."

U.S. Pat. No. 3,527,709, for "FLUORESCENT TRACER PROCESS AND COMPOSITIONS."

U.S. Pat. No. 3,530,295, for "TRACER PROCESSES EMPLOYING ULTRAVIOLET ABSORBER MATERIALS."

U.S. Pat. No. 3,557,015, for "DUAL-SENSITIVITY DYED LIQUID TRACERS".

U.S. Pat. No. 3,697,598, for "INSPECTION PENETRANT PROCESS AND COMPOSITIONS EMPLOYING MIXTURES OF FLOURESCENT INDICATOR DYE AND NON-FLUORESCENT ULTRAVIOLET ABSORBER DYE." U.S. Pat. No. 3,931,733, for "METHOD AND MEANS OF ACCELERATING REMOVAL OF BACKGROUND ENTRAPMENTS IN THE INSPECTION PENETRANT PROCESS."

U.S. Application No. 577,323, filed May 14, 1975, for "INSPECTION PENETRANT PROCESS USING SOLVENCY-INHIBITED REMOVER COMPOSITIONS", now U.S. Pat. No. 3,992,319.

U.S. Application Ser. No. 606,285, filed Aug. 20, 1975, for "METHOD OF REGENERATING AN INSPECTION PENETRANT SOLVENT," now U.S. Pat. No. 3,988,924.

U.S. Pat. No. 3,896,664, for "ENHANCED STABILITY WATER WASHABLE PENETRANT COMPOSITION AND PROCESS".

The present invention relates to a method and means of restoring and regenerating the solvent activity of a water-diluted glycol-ether solvent-remover composition, and purifying and recovering the solvent remover for re-use by means of solvent extraction of any dissolved penetrant material.

In my above-mentioned U.S. Application Ser. No. 577,323, I have disclosed and claimed solvency-inhibited remover compositions which may be employed to dissolve and remove excess surface penetrant and unwanted micro-porosity entrapments of penetrant from test surfaces. In my subsequent U.S. application Ser. No. 606,285, now U.S. Pat. No. 3,988,924, of which the present application is a continuation-in-part, I have disclosed and claimed a process of regenerating and recovering a solvent remover composition where the glycol-ether type ingredient of the composition is selected for its characteristic of solubility-inversion at elevated temperatures.

Normally, in the solvent-remover-type penetrant process, a water-insoluble dyed liquid penetrant is applied to a test surface being inspected for the presence of crack defects. The dyed penetrant enters any cracks or flaws which are open to the surface, forming penetrant entrapments. Excess surface penetrant is removed from the test surface by draining, wiping, or pre-rinsing with a spray of water, and finally by applying a solvent remover such as alcohol, mineral thinner, or halocarbon liquid, which acts to dissolve surface of residues of penetrant and flush them away. Entrapments of dyed liquid penetrant which migrate out of the surface flaws, or which are developed by absorption onto a coating of powder-type developer, may be detected visually by examination under black light in the case of fluorescent indicator dyes, or under white light in the case of visible-color indicator dyes.

A difficulty is inherent in the conventional solvent-remover inspection penetrant process, in that the solvent action of the solvent remover is so rapid that significant crack entrapments of penetrant are often stripped out within a few seconds or even within a fraction of a second following application of the solvent remover. In other words, the conventional solvent remover materials are difficult to control, since they act much too rapidly in removing surface penetrant from test parts.

The inhibited-solvency removers which are disclosed and claimed in my copending U.S. application Ser. No. 577,323 provide a retarded solvent action so that ample time is allowable for applying the inhibited-solvency remover to test surfaces, and for cleaning and drying the test surfaces, without an excessive stripping out of desired crack entrapments. A means for accomplishing this partial and controlled inhibition of solvent remover action is to utilize a water-soluble solvent remover or solvent-coupler material and to dilute the material with water so as to provide a specified concentration of active solvent in the water. The active solvents, or solvent couplers, utilized in the afore-said U.S. application Ser. No. 577,323, may be drawn from a group including various alcohols, glycols, and glycol-ethers, and the concentrations utilized may range from less than 5% up to as much as 75% or more.

In the inhibited solvent-remover process, test parts or test surfaces are first treated with a dyed oily penetrant liquid. Usually, the penetrant contains a fluorescent indicator dye, but in some cases it may contain a visible-color dye such as red for example.

As a second step in the inhibited solvent-remover process, test surfaces are usually "conditioned" by spraying them, with water for the purpose of stripping off thick-film coatings of penetrant. The thus-removed penetrant is separated from the wash water by flotation and is thus recovered for re-use. Test surfaces which are conditioned in this manner retain only relatively small residues of penetrant which may be in the form of thin-film smears or porosity entrapments.

A third step in the process involves removal of thin-film residues of penetrant and porosity entrapments from the test surfaces. The object here is to remove unwanted background indications, smears, etc., which may interfere with the see-ability of actual crack indications. This is accomplished by rinsing or spray-washing the test surfaces with a slow-acting water solution of a glycol-ether solvent-coupler, such as ethylene glycol monobutyl ether or diethylene glycol monobutyl ether. The activity or solvent strength of the slow-acting remover is adjusted to a desired characteristic by adjusting the dilution ratio of the glycol/water mixture.

The oily penetrant is normally insoluble or only slightly soluble in plain water, but is somewhat more soluble in a dilute solution of a glycol-ether solvent. Various dilution ratios may be employed for the glycol-ether solvent remover, ranging from as little as 2 – 1 up to as much as 200 – 1.

The final step, or combination of steps, in the process involves drying the test parts, developing crack indications, and inspecting the test surfaces for such indications. Sometimes, self-development is employed, where crack entrapments of penetrant are allowed to exude merely by setting the test parts aside for five or ten minutes. In some other cases, a powder-type developer may be used to draw out crack entrapments of penetrant by capillary attraction.

When solvency-inhibited water solutions of the type disclosed and claimed in my U.S. application Ser. No. 577,323 are used to dissolve and remove penetrant from test parts, they soon become contaminated with dissolved penetrant and dyes, and gradually lose their solvent strength. In the past, it has been necessary to discard such used materials, but it would be beneficial from the standpoint of economy in chemical consumption as well as avoidance of pollution of sewage systems to regenerate and re-use the exhausted solvency-inhibited remover materials.

The principal object of the invention, therefore, is to provide a method and means for recovering and re-using solvency-inhibited remover materials.

Another object of the invention is to provide a method and means of selectively extracting penetrant contaminants from a solvent remover consisting of a dilute solution of glycol-ether in water.

These and other objects of the invention will in part be obvious and will in part become apparent from the following description thereof.

I have discovered that any of the normally liquid halocarbon solvents, such as chlorinated hydrocarbons or chlorinated-fluorinated hydrocarbons, will act to extract penetrant contaminants from glycol-ether/water mixtures. Extraction solvents of this kind may be enumerated as in the following partial listing.

1.1.2.2-Tetrachloroethane
1.1.2.2-Tetrachloroethylene (Perchloroethylene)
1.1.2-Trichloroethane
1.1.2.2-Tetrachloro-1.2-difluoroethane (Freon BF)
1.1.1.2-Tetrachloro-2.2-difluoroethane
1.1.2-Trichloroethylene
Carbon tetrachloride 1.1.1-Trichloroethane
Chloroform
1.1.2-Trichloro-1.2.2-trifluoroethane (Freon TF)
1.1.1-Trichloro-2.2.2-trifluoroethane
Methylene chloride
Trichlorofluoromethane (Freon MF)

Halogenated hydrocarbons, such as are listed above, are all effective solvents for oily liquids of the kind which are used in solvent-remover-type inspection penetrants. Such oily liquids may be of the type disclosed and claimed in my above-mentioned U.S. Pat. No. 3,311,479, or my U.S. Pat. No. 3,896,664, or they may be simple mineral oils having sufficient aromaticity to maintain the indicator dye or dyes in solution. Some of the preferred oily liquids for such usage are dimethyl naphthalene, dioctyl phthalate, nonylphenol, or 2,2,4-Trimethyl-1,3-pentanediol-diisobutyrate.

With regard to the glycol-ether material which may be used as a constituent in the dilute glycol-ether/water mixture, there are a number of glycol-ether compounds which have a mutual solvent capability for penetrant oils and water. I have found, however, that most glycol-ether compounds are capable of being extracted from water solutions by halogenated hydrocarbons, at least to a noticeable degree. The result of such a solvency response is that the dilution ration of the glycol-ether/water mixture becomes altered as the mixture is passed through a column of extraction solvent.

I have discovered that there at least five glycol-ether compounds which when in water solution are essentially inert to the solvent action of halogenated hydrocarbons. These inert materials may be enumerated as follows:

Ethylene glycol methyl ether (Dowanol EM)
Ethylene glycol ethyl ether (Dowanol EE)
Diethylene glycol methyl ether (Downanol DM)
Diethylene glycol ethyl ether (Dowanol DE)
Propylene glycol methyl ether (Dowanol PM)

Thus, if the solvent remover for the inhibited solvent remover process is prepared from any one or a combination of the above-identified glycol ethers, the remover mixture may be clarified and regenerated efficiently by bubbling the used mixture through a column of halogenated hydrocarbon liquid. Penetrant contaminants are selectively extracted, and the dilution ratio of the glycol-ether/water mixture is not disturbed or altered. The consequence of using one of the glycol-ethers of the invention is that the solvent remover mixture may be cycled repeatedly through a solvent-extraction column, being continuously restored to a re-usable condition.

I have found that the glycol-ethers of the invention may be used in water mixtures at dilution ratios ranging from about 2 – 1 up to 300 –1 or more, and they will still be inert to the extraction solvent, that is with respect to changes in dilution ratio.

Accordingly, the invention represents an improvement in the so-called inhibited solvent remover penetrant process, and consists of the step of circulating a dilute solution of a glycol-ether, as identified above, through a column of normally liquid halocarbon solvent. The halogenated hydrocarbon liquids are heavy, so that as the glycol-ether/water mixture is injected at the bottom of the extraction column the water mixtures bubbles up to the surface of the extraction solvent and is returned to the remover processing tank. Extracted penetrant contaminants remain in the extraction solvent until the solvent becomes highly concentrated, at which point it may be drawn off and distilled to separate out and recover the penetrant, while restoring the extraction solvent to full strength.

It will be understood that I make no restriction with respect to the type of oily penetrant which is utilized in the solvent-remover process, so long as it is insoluble in water, or nearly so, and contains little or no detergent ingredients. Likewise, I make no restriction on the halogenated hydrocarbon liquid which is utilized as an extraction solvent, except that I prefer such solvents as methylene chloride, 1.1.1-trichloroethane, and perchloroethylene.

I have found that the inhibited solvent remover compositions of the invention may be modified by the addition of a surfactant ingredient, and the remover mixture will still be relatively inert to solvent action by the halogenated hydrocarbons. For example, a remover mixture may be prepared by starting with a concentrate consisting of a mixture of equal parts of glycolether and a water-soluble surfactant liquid such as 9-mol ethoxylated nonylphenol. The concentrate is mixed with water to a dilution ration which may range from about 5 – 1 up to as much as 250 – 1. The effect of the surfactant ingredient is to accelerate the solvent action of the remover mixture in removing residues of penetrant from test surfaces.

Any water-soluble surfactant material may be used in combination with the glycol-ethers of the invention, and many hundreds of such materials are available in the industry. The relative proportion of the surfactant, with respect to the glycol-ether, may range from zero up to about two parts surfactant to one part glycol-ether.

The surfactant ingredient acts to emulsify the extraction solvent to a certain extent, and thus interfere with the rapid and clean separation and extraction of penetrant contaminants. Therefore, preferred solvent remover mixtures contain relatively small amounts of surfactant, not more than equal parts by volume relative to the glycol-ether constituent.

It will be understood, therefore, that I make no restriction as to the type or quantity of surfactant material which is used in the remover compositions of the invention, except as an excessive proportional amount of such surfactant may interfere with the proper operation of the extraction column.

I have found that in cases where the glycol-ether/water mixture remover compositions of the invention are modified by the addition of a surfactant material as described above, the preferred extraction solvent is methylene chloride. This is because such glycol-ether/surfactant/water mixtures have very little tendency to form emulsions when bubbled through a column of methylene chloride. Methylene chloride does have a very slight solubility in water, so that it becomes gradually carried over into the dilute solvent remover mixture as the solvent remover is circulated through it. However, the methylene chloride which remains in the extraction column acts to selectively extract any dissolved penetrant and dyes, leaving the solvent remover mixture restored to a re-usable condition.

After prolonged usage and circulation of the solvency-inhibited remover solutions of the invention through the extraction column containing a halocarbon liquid, the layer of halocarbon liquid may accumulate a relatively high concentration of penetrant and dye materials. This solution may be bled off and discarded, being replaced with fresh halocarbon liquid, or alternatively a suitable still device may be utilized to purify and recover the halocarbon liquid.

Accordingly, the method and means of the invention may include several supplementary steps of distillation-recovery of the bottom layer of halocarbon extraction solvent. In practice, the accumulation of contaminants in the bottom layer of extraction solvent takes place very slowly, so that the rate of distillation vapor transfer of this bottom layer material may also take place very slowly. A practical purifier still for a typical clarifier outfit may consist of a small tubular still chamber having a volume of less than a gallon of liquid. A few hundred watts of heat power, or less, may be introduced into this still chamber to produce vaporization of the extraction solvent, leaving nonvolatile penetrant oils and dyes in the still chamber. It will be understood that distillation may be made to proceed more rapidly by increasing the power input to the still. I place no limitations on the rate of distillation, since this may depend on the rate at which contaminating substances accumulate in the bottom liquid layer in the extraction column.

The inhibited-solvency remover solutions of the invention are characterized by relatively low solvent strengths, as compared with conventional solvent remover materials, and they will not dissolve large quantities of penetrant oils and dyes from test surfaces. Accordingly, test surfaces must be properly prepared before treatment with the inhibited-solvency remover, so as to mechanically remove the bulk of the surface penetrant, leaving only extremely thin residual films of penetrant and entrapments of penetrant in surface cracks and micro-porosities. This kind of pre-treatment may be effected by spraying the penetrant-coated test surface with plain water so as to flush off the bulk of the surface of the penetrant. The thus-removed penetrant floats to the surface and is collected for re-use. This technique of pre-rinse removal and recovery of water-insoluble penetrants is frequently employed in penetrant processes, and is well known in the art.

I have found it possible to measure the effective average film thickness of a given fluorescent penetrant residue which remains on a test surface after a pre-rinsing treatment. A convenient method for making such measurements is to calibrate the penetrant with respect to its dimensional threshold of fluorescence transition, and then measure the apparent brightness of penetrant residues of porosity entrapments on the test surface. Calibration precedured and measurement methods of these kinds are set forth in my U.S. Pat. Nos. 3,107,298 and 3,341,705.

I have found that in the case of test parts such as JO-coated jet engine turbine blades, which exhibit severe surface porosity conditions, the equivalent residual film thickness of penetrant in porisity entrapments after pre-rinse treatment is typically about 0.2 microns. Many other parts, such as nickel-chrome castings, may exhibit residual films of penetrant after prerinsing of about 0.01 micron. Highly polished surfaces, which are rarely encountered in industrial inspection, may show negligible surface residues of penetrant after-pre-rinsing, or they may show substantial surface residues, depending on the nature of the penetrant which is employed.

In any event, following a properly applied step of pre-rinsing, the amount of penetrant which remains on a given test surface is quite small, even though it may show an extremely pronounced background of fluorescent indications, which background is often sufficient to completely obscure any actual crack indications which may be present.

It is these unwanted background indications and smears of penetrant residues which must be removed by solvent action of a remover, and I have found that water solutions of the glycol-ether materials of the invention will provide adequate solvent action, or rate of solution removal, at dilution ratios within the range of from about 1 — 1 up to about 200 – 1.

It will be understood that the method and means of the present invention first of all involves the use of specified glycol-ether materials dissolved in water to desired concentrations. Second, it will be understood that a process step (a) must be carried out, this step being the continuous circulation of the glycol-ether/water mixture through a column of halocarbon extraction solvent.

The afore-said process step serves to provide a continuous regeneration and clarification of the solvent remover solution, so that it may be used and re-used in a solvency-inhibited-remover inspection penetrant process. It will be understood that supplemental steps of distillation may be carried out in repetitive rotation so as to extract and remove penetrant oils, dyes, and other dissolved materials from the bottom layer of halocarbon liquid in the extraction column, these steps being:

b. Withdraw liquid from the bottom layer in the extraction column into a still chamber.
c. Introduce heat energy into the still chamber to vaporize the halocarbon extraction solvent.
d. Condense the halocarbon vapors, and return the thus-condensed liquid to the extraction column.
e. Drain off and discard accumulations of nonvolatile penetrant oil, dye residues, and sludge from the still chamber, or recover such penetrant material if it is re-usable.

The extraction column along with a still chamber, is such is employed, may be enclosed and sealed, leaving as the only vapor outlet a reflux condenser coil. This coil may be air cooled so as to maintain it at a suitable low temperature such as room temperature. In this way, no vapors of any kind can escape from the apparatus beyond what might be produced by the normal room-temperature vapor pressure of the glycol-ether and water ingredients. Some of the processing materials will be lost by carry-over or drag-out on test parts and in entrapments in the test parts as they are processed. However, for all practical purposes, the regenerating and recovery apparatus of the invention may provide an effectively closed circuit, except for small losses from drag-out and evaporation. p In view of the fact that some carry-over and evaporation loss of solvent remover solution occurs during the processing of test parts, it will be found necessary to replenish the solution reservoirs from time to time. A small extraction column reservoir having a volume of about 5 gallons may be entirely adequate to provide clarification and regeneration of remover solution stored in a processing tank containing several thousand gallons of remover solution. The same 5 gallon extraction column unit may be used in conjunction with small remover dip tank having a volume of 10 gallons or less of remover solution. A single small extraction column may be employed to purify and regenerate a large volume of remover solution in a central reservoir tank, and this solution may be piped out to a number of processing and inspection stations in a given production facility.

When used as a solvent remover in an inspection penetrant process, the solvent remover solution of the invention may be applied to test parts by dipping, spraying, or otherwise flooding the test surfaces being processed. In any event, the used remover is drained from the test surfaces, and is ultimately returned to the solvent extraction clarifier unit where it is regenerated for re-use.

I have found that for many kinds of test parts such as jet engine turbine blades, or other aircraft parts, a concentration of about 10 to 20% of diethylene glycol ethyl ether in water is about optimum for the purpose of providing a desired remover contact time in the range of about 2 to 4 minutes at room temperature. In many cases, it may be desired to operate the remover mixture at an elevated temperature in the range of from 90° to 110° F. For such usage, the remover mixture may be heated and thermostatically controlled to such desired temperature, and the concentration of the glycol-ether ingredient would be reduced to a point where an appropriate rate of removal is provided.

Diethylene glycol ethyl ether is a preferred material for use as a solvent remover in the process of the invention. One benefit which is derived from the use of this preferred material is that it is reasonably volatile and will evaporate from test surfaces even at room temperature. Thus, after test parts are treated in the inhibited-solvency remover solution for the required contact time duration, they may be drained and dried by blowing off excess liquid using a compressed air gun, or the parts may be dried under a warm-air blower or in an oven. Where the working solutions are maintained at an elevated temperature, test parts retain enough heat so that they tend to dry rapidly when excess liquid is blown off of the surfaces. In any event, the parts may dry rapidly, leaving well-defined flaw entrapments.

The method and means of the present invention may be employed in conjunction with any of the conventional water-insoluble post-emulsifiable-type inspection penetrants, however the preferred penetrant materials are of the types which are disclosed and claimed in my U.S. Pat. No. 3,311,479. Penetrants of these kinds employ liquid vehicles which are relatively nonvolatile, although there exists a wide variety of suitable liquids which have differing boiling ranges.

It will be understood that some post-emulsifiable-type penetrants have low boiling points, and they are therefore not readily adaptable to distillation-separation from the extraction solvent materials of the invention. When such penetrant materials are employed, they mat be allowed to accumulate in the bottom layer of the extraction column, ultimately being bled off and discarded. Most of my preferred penetrant compositions, as taught in my U.S. Pat. No. 3,311,479, are characterized by high boiling points and low vapor pressures, so that they are easily separated by distillation from the halocarbon extraction solvent materials of the invention.

The penetrant materials which are employed in conjunction with the solvency-inhibited removers of the invention may utilize any of the known types of indicator dyes. Visible-color indicator dyes may be used, but the preferred indicator dyes are fluorescent in character. Furthermore, these fluorscent dyes are preferably employed at high concentrations, in accordance with the teachings of my U.S. Pat. No. 3,386,920, now U.S. Pat. No. Re. 26,888, at concentrations sufficient to provide dimensional thresholds of fluorescence smaller than about 250 millimicrons.

I have noticed that certain of the fluorescent dyes which are commonly used as indicators in inspection penetrants, notably the coumarin-type dyes, exhibit a certain degree of solubility in water. This effect of solubility causes the dye to be leached out of penetrant entrapments in crack defects during the step of remover application, even though the penetrant liquid itself remains in he crack. Certain other types of fluorescent substances, such as those which are disclosed and claimed in my U.S. Pat. No. 3,527,709, are characterized by much lower water-solubility, and are thus capable of providing an improved resistance to leaching.

Actually, the selection of the indicator dye may often be a matter of preference, without regard to features of solubility or leaching.

In some inspection applications, it may be desired to employ a combination of visible-color and fluorescent indicator dyes in order to provide an effect of dual-sensitivity in the penetrants. Thus, for such purposes, dye combinations of the types disclosed and claimed in my U.S. Pat. No. 3,557,015 may be employed in penetrants utilized in the process of the invention. Likewise, combinations of fluorescent and ultraviolet absorber dyes, as taught and claimed in my U.S. Pat. No. 3,697,598, or even ultraviolet absorber dyes alone, as taught and claimed in my U.S. Pat. No. 3,530,295, may be used in the penetrants employed in the process of the invention.

It will be understood that considerable variations may be encountered in optimum processing times and temperatures, depending on the preference of the user, the processing equipment which is available, the kinds of parts being processed, and other factors which may enter into consideration. For these various and combined reasons, it may be desired to operate the remover solutions of the invention at concentrations of the glycol-ether material as low as 0.5% or as high as 50% or even more. I therefore place no limits on processing conditions or concentrations of the solvent remover solutions which may be applicable.

It will be further understood that the method and means of the present invention may be combined with various other process steps which have not been specifically mentioned herein. For example, the processing sequence of pre-rinsing, solvent remover application, and final drying may be interrupted to introduce one or more steps of interim-drying in accordance with the teachings of my U.S. Pat. No. 3,931,733.

Also, it will be understood that various additive substances may be included in the solvent remover solutions of the invention. For example, it may be desired to increase the viscosity of the solvent remover solution, in which case a thickener substance may be added. Suitable thickener materials may be any one of the sodium carboxymethylcellulose polymers, known commercially as "CMC". Another type of thickener gum is poly (methyl vinyl ether/maleic anhydride), known commercially as "Gantrez AN". Both of these materials are soluble in cold or hot water, and will remain in water solution in the presence of substantial amounts of the glycol-ether materials of the invention. They are both available in a range of molecular weights, the preferred molecular weights being the higher values which provide high solution viscosities at low concentrations.

Many of the conventional water-soluble gums, such as methyl cellulose or ethyl hydroxyethyl cellulose, tend to precipitate from solution at elevated temperatures or in the presence of added glycol-ether materials, and these are therefore unsuitable as thickeners. For the water-soluble gums which are suitable for use in the remover solutions of the invention, it is usually possible to achieve a satisfactory increase in viscosity at gum concentrations in the range of about 0.2% up to about 3%.

Although the invention has been described with respect to specific embodiments thereof, it will be understood that various changes and modifications may be made without departing from the spirit of the invention and the scope of the appended claims.

I claim:

1. In an inspection penetrant process which includes the steps of (1) applying a water-insoluble dyed liquid pentrant to test surfaces, (2) applying a solvent remover to said penetrant-treated test surfaces to dissolve and remove excess surface penetrant, leaving entrapments of penetrant in any surface cracks which may be present, and (3) inspecting said test surfaces for the presence of flaw-entrapment indications, the improvement which comprises the following step
    a. After using said solvent remover to dissolve dyed liquid penetrant from said test surfaces, withdraw the said used remover from a remover reservoir tank and circulate it through a column of halogenated hydrocarbon extraction solvent, returning said used remover to said remover reservoir tank, said solvent remover comprising a mixture in water of a glycol-ether solvent liquid which is substantially inert to extraction from water solution, said glycol-ether liquid being present in the water mixture at dilution ratios from about 2 – 1 up to about 300 – 1 by halogenated hydrocarbon extraction solvent.

2. A method in accordance with claim 1, in which supplemental steps of distillation are carried out in repetitive rotation as follows:
    b. Withdraw liquid from a bottom layer of said extraction column into a still chamber.
    c. Introduce heat energy into said still chamber to vaporize said halogenated hydrocarbon extraction solvent.
    d. Condense said halogenated hydrocarbon vapors, and return the thus-condensed liquid to the said extraction column.
    e. Drain off and discard accumulations of nonvolatile penetrant oil, dye residues, and sludge from said still chamber.

3. A method in accordance with claim 1, in which said glycol-ether liquid is at least one member selected from the group consisting of ethylene glycol methyl ether, ethylene glycol ethyl ether, diethylene glycol methyl ether, diethylene glycol ethyl ether, and propylene glycol methyl ether.

4. A method in accordance with claim 1, in which said glycol-ether is diethylene glycol ethyl ether.

5. A method in accordance with claim 1, in which the concentration of said glycol-ether liquid in said remover solution is adjusted to a value within the range of from about 50 down to about 0.5%.

6. A method in accordance with claim 1, in which said remover mixture contains an added water-soluble thickener gum to a concentration within the range of about 0.2 up to about 3%.

7. A method in accordance with claim 1, in which said extraction solvent is at least one member selected from the group consisting of methylene chloride, 1.1.1-trichloroethane, and perchlorethylene.

8. A method in accordance with claim 1, in which said solvent remover contains a water-soluble surfactant additive, said water-soluble surfactant being present in a relative proportion with respect to said glycol-ether solvent liquid ranging from zero to about two parts surfactant to oen part glycol-ether.

* * * * *